United States Patent
Fox et al.

(10) Patent No.: US 9,766,191 B2
(45) Date of Patent: Sep. 19, 2017

(54) XRF DEVICE WITH TRANSFER ASSISTANCE MODULE

(71) Applicant: TRIBOGENICS, INC., Los Angeles, CA (US)

(72) Inventors: Dale Fox, Los Angeles, CA (US); Thomas Michael Schurman, Woodland Hills, CA (US); Justen Lee Harper, Turlock, CA (US)

(73) Assignee: Tribogenics, Inc., Los Angeles, CA (US)

( * ) Notice: Subject to any disclaimer, the term of this patent is extended or adjusted under 35 U.S.C. 154(b) by 227 days.

(21) Appl. No.: 14/814,419

(22) Filed: Jul. 30, 2015

(65) Prior Publication Data

US 2016/0033430 A1 Feb. 4, 2016

Related U.S. Application Data

(60) Provisional application No. 62/031,102, filed on Jul. 30, 2014.

(51) Int. Cl.
*G01N 23/223* (2006.01)
*H04W 4/04* (2009.01)
(Continued)

(52) U.S. Cl.
CPC ....... *G01N 23/223* (2013.01); *G06Q 30/0645* (2013.01); *H04W 4/021* (2013.01); *H04W 4/04* (2013.01)

(58) Field of Classification Search
CPC ........... G01N 23/223; G01N 2223/076; G01N 2223/301; G01N 23/2204;
(Continued)

(56) References Cited

U.S. PATENT DOCUMENTS 7,496,178 B2 * 2/2009 Turner ................ A61B 6/4405
378/101
7,875,847 B2 * 1/2011 Dugas ............. G01N 35/00732
250/281

(Continued)

FOREIGN PATENT DOCUMENTS

JP 2004-093511 3/2004
KR 10-2008-0050405 6/2008

OTHER PUBLICATIONS

International Search Report on related PCT Application No. PCT/US2015/043016 from International Searching Authority (KIPO) dated Nov. 25, 2015.

(Continued)

*Primary Examiner* — Hoon Song
(74) *Attorney, Agent, or Firm* — Klein, O'Neill & Singh, LLP

(57) ABSTRACT

A handheld x-ray fluorescence (XRF) device may include communication circuitry for communicating over a network. In some embodiments information related to sale and/or pricing of material identified by the XRF device is communicated by and/or to the XRF device. In some embodiments the XRF device communicates information regarding rental of the XRF device. In some embodiments the XRF device may be used to ascertain whether an item, for example an item of evidence or a particular item in a manufacturing environment, includes a material composition expected for the item, and in some embodiments storing or logging a result of such a determination.

18 Claims, 8 Drawing Sheets

(51) Int. Cl.
*H04W 4/02* (2009.01)
*G06Q 30/06* (2012.01)

(58) Field of Classification Search
CPC ......... G01N 2223/633; G01N 23/2076; G01N 2223/0766; G01N 2223/303; G01N 2223/61; G06Q 30/0645; G06Q 30/02; G06Q 20/387; G06Q 20/204; G06Q 30/0207; G06Q 30/0226; G06Q 30/0233; G06Q 40/00; G06Q 20/24; G06Q 20/34; G06Q 30/00; H04L 63/10
See application file for complete search history.

(56) References Cited

U.S. PATENT DOCUMENTS

| | | |
|---|---|---|
| 2008/0205593 A1 | 8/2008 | Yellepeddi |
| 2010/0080351 A1 | 4/2010 | Hession-Kunz et al. |
| 2010/0299161 A1* | 11/2010 | Burdick ................. G06Q 40/08 705/4 |
| 2011/0214050 A1* | 9/2011 | Stambaugh ......... G06F 3/04817 715/234 |
| 2013/0077754 A1 | 3/2013 | Sasaki et al. |

OTHER PUBLICATIONS

Written Opinion on related PCT Application No. PCT/US2015/043016 from International Searching Authority (KIPO) dated Nov. 25, 2015.

\* cited by examiner

XRF DEVICE WITH TRANSFER ASSISTANCE MODULE

CROSS REFERENCE TO RELATED APPLICATIONS

This application claims the benefit of U.S. Provisional Patent Application No. 62/031,102, filed on Jul. 30, 2014, entitled XRF Device with Transfer Assistance Module, the disclosure of which is incorporated by reference herein.

BACKGROUND OF THE INVENTION

The present invention relates generally to material identification and transfer, and more particularly to x-ray fluorescence devices and deployment and material transfer assistance modules.

X-ray fluorescence (XRF) devices are often used to determine composition of materials. In general, XRF devices generate x-rays to strike a sample, and analyze return radiation from the sample to determine material composition of the sample. Handheld XRF devices may be used in the field, providing mobility in identifying materials of interest.

Unfortunately, XRF devices may not always be in hand when identification of materials is desired, and identification of the materials of interest does not necessarily inform as to what may be done with the materials, or how such an action may be accomplished.

BRIEF SUMMARY OF THE INVENTION

In some embodiments a handheld XRF device generates x-rays, receives return radiation from a sample struck by those x-rays, analyzes the return radiation to determine a material of the sample, transmits (using communication circuitry included with the device or data linked to the device) information indicating the material over a communication network to a server, receives information from the server relating to potential purchasers of the material and/or prices of or for the material, transmits information regarding a potential sale of the material to at least one of the potential purchasers, and, in some embodiments, receives an offer to purchase (or an acceptance of an offer to sell) the material from at least one of the potential purchasers. Information received from the server and/or potential purchasers may be displayed on a display of the XRF device.

In some embodiments the device additionally includes a camera, and the device provides an image of the material to at least one potential purchaser. In some embodiments the device additionally includes a printer, for example for printing a tag or label, which may be used for example to print a tag for the material. In some embodiments the device additionally includes a geographic location determination circuitry such as GPS circuitry, and in some embodiments device location information is also provided to the server and, in some embodiments, to the potential purchasers. In some embodiments the device location information is used by the server to determine information of potential purchasers to provide to the device. In some embodiments the information provided by the server indicates physical properties of the material, safety information related to the material, and/or other information related to the material. Information about the user, usage, and other data gathered can provide trends and other useful insight to better serve the user and industry.

Some embodiments provide a handheld x-ray fluorescence (XRF) device, comprising: an x-ray source; a detector for detecting a return signal and circuitry for processing the return signal to determine material composition of a sample struck by x-rays of the x-ray source; cellular communication circuitry; a display; and a processor configured by program instructions, the program instructions including program instructions to: provide information regarding the material composition of the sample to the cellular communication circuitry for transmission, receive information regarding pricing of the sample, and format the information regarding pricing of the sample for display by the display.

Some embodiments provide a method of operation of a handheld x-ray fluorescence (XRF) device, comprising: activating an x-ray source of the handheld XRF device; detecting a return signal; processing the return signal to determine material composition of a sample struck by x-rays of the x-ray source; providing information regarding the material composition of the sample to communication circuitry for transmission; transmitting the information regarding the material composition of the sample over a network; receiving information regarding pricing of the sample, and displaying the information regarding pricing of the sample by a display of the XRF device.

Some embodiments provide a method of providing handheld x-ray fluorescence (XRF) device rental availability information, comprising: receiving an indication of XRF device location; receiving an indication of XRF device rental price; receiving an indication of XRF device time of availability; transmitting, by the XRF device, the XRF device location, XRF device rental price, and XFR device time of availability over a network. In some embodiments usage of the XRF device can be controlled remotely. For example, the XRF device can be time-locked remotely based on the rental or service agreement. In other examples, the XRF device can be time-locked on the device itself.

Some embodiments provide a method of operation of a handheld x-ray fluorescence (XRF) device, comprising: receiving an item identification for an item, including an identification of material of the item; activating an x-ray source of the handheld XRF device; detecting a return signal; processing the return signal to determine material composition of a sample struck by x-rays of the x-ray source; determining whether the material composition of the sample matches the identification of material of the item; and storing a result of the determination of whether the material composition of the sample matches the identification of material of the item.

These and other aspects of the invention are more fully comprehended upon review of this disclosure.

DETAILED DESCRIPTION

Figure 1A:
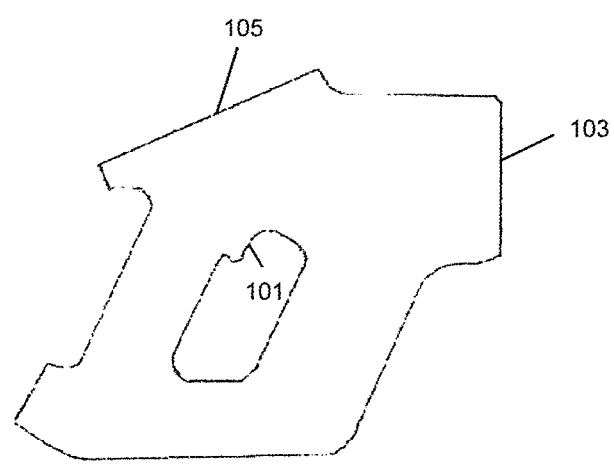
FIG. 1A illustrates, in outline form, a handheld XRF device in accordance with aspects of the invention.

FIG. 1A illustrates, in outline form, a XRF device. In some embodiments, the XRF device is portable or handheld. The XRF device includes a trigger 101 or other activation mechanism for activating an x-ray source within the device, with x-rays generally exiting the device about a forward portion 103 of the device. A detector in the device receives radiation from a sample about the forward portion of the device, with circuitry of the device configured to determine material composition of the sample, or information for determining material composition of the sample. In some embodiments, the circuitry of the device configured to determine material composition of the sample, or information for determining material composition of the sample is performed by the processor. In the embodiment of FIG. 1A, the handheld XRF device additionally includes a display 105, communication circuitry, for example cellular communication circuitry, GPS circuitry, and, in some embodiments, printer circuitry and associated printer hardware. In some embodiments the XRF device can include an RFID sensor, Bluetooth communications, and/or a laser pointer system to determine geographic location. In some embodiments the XRF device may be powered by a battery in the XRF device or supplied to the XRF device.

Figure 1B:
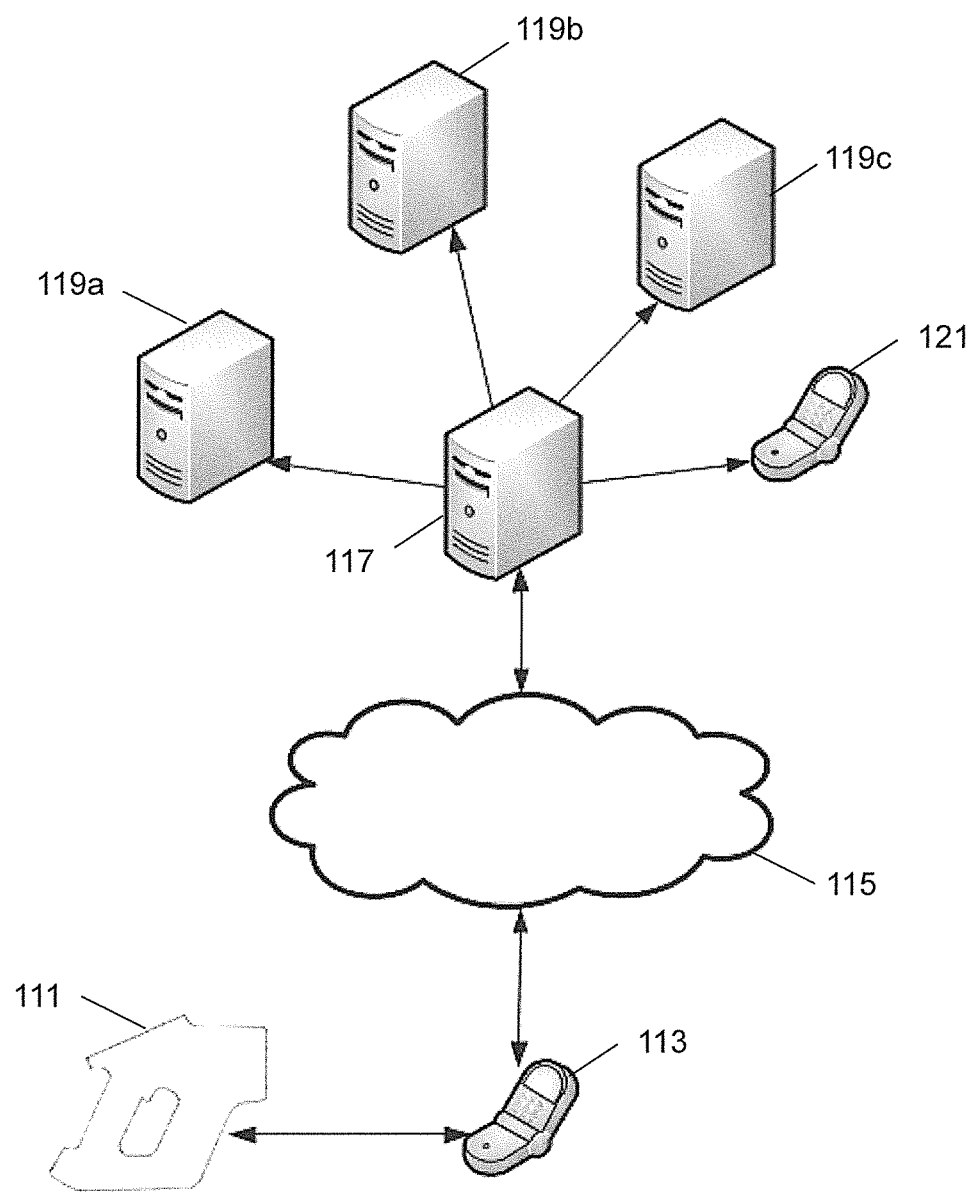
FIG. 1B illustrates a network model useful with aspects of the invention.

FIG. 1B shows a network model, with a handheld XRF device 111 shown as part of a network. In some embodiments the XRF device of FIG. 1B is the XRF device of FIG. 1A, and the XRF device is communicatively coupled to a wide area network 115, which may be the Internet. As illustrated in the example of FIG. 1B, the XRF device is in data communication with a smartphone 113, which in turn is communicatively coupled to the wide area network 115, which may be the Internet. Communications between the XRF device and the smartphone may be by way of wired or wireless communications. In addition, although the XRF device and the smartphone are shown in FIG. 1B as physically separate devices, in some embodiments the smartphone, or relevant portions of the smartphone, may be physically part of or embodied within the XRF device. For example, similar to the XRF device of FIG. 1A, in some embodiments some or all of a cellular and/or other wireless communication capability, a display, user input device (e.g. touchscreen), and GPS receiver circuitry may be part of the XRF device. In addition, in some embodiments the smartphone may be mounted, removably or otherwise, to the XRF device.

The XRF device generally includes an x-ray source which may be selectively activated, for example by way of a trigger or other user input, a detector for detecting return signals, and circuitry for processing the return signal to determine material composition information of a sample. In operation, generally a user directs the device such that x-rays will be directed at a sample of unknown composition, and activates the x-ray source. The sample can be in any form or phase such as gases, liquids, solids, powders, or any combination of phases. As the x-rays strike the sample, a return signal is generated, which is detected and processed by the detector and circuitry to provide sample material composition information.

The material composition information may be communicated to the smartphone, which may be configured, for example by program instructions, to transmit the material composition information, or information relating to the material composition information, over the network 115 to a server 117. The server in turn may transmit the material composition information, or other information, to other compute devices, for example computers 119a-c and smartphone 121 as shown in FIG. 1. In various embodiments the computers 119a-c and smartphone 121 may also transmit information to the server 117, for processing and/or for relaying to the smartphone 113 or XRF device.

In some embodiments the XRF device and/or smartphone communicate material identification information to the network, and in some embodiments the material identification information comprises an identification of a metal or metal alloy of the material. In some embodiments, material identification can also include elemental analysis for trace element or trace element detection, as well as variances on the make-up or composition of materials under analysis. In some embodiments the XRF device and/or smartphone communicate an identification of the metal or metal alloy and an indication of quantity of the metal or metal alloy, for example a weight. In some embodiments the XRF device and/or smartphone additionally transmit location information of the metal or metal alloy, with the location information derived from a GPS receiver of the XRF device and/or smartphone. In some embodiments location information can also be derived from other location-based electronic measures such as low energy Bluetooth and RFID. Material and user location information can be monitored and gathered.

In some embodiments the XRF device and/or smartphone receive pricing information for the metal or metal alloy from the network. In some embodiments the XRF device and/or smartphone receive offers to purchase the metal or metal alloy from the network. In some embodiments, advertisements may also be received by the XRF device and/or smartphone.

In some embodiments the XRF device provides an indication of availability of the XRF device for use by third parties to the network. In some such embodiments the XRF device also provides an indication of location of the XRF device. In some embodiments the XRF device provides a price for use by third parties.

Figure 2:
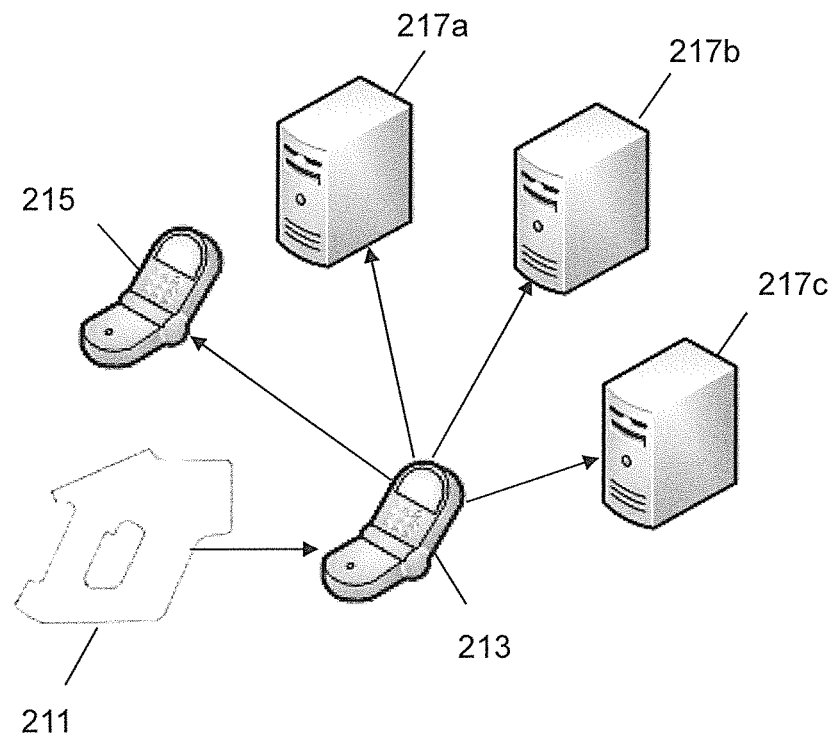
FIG. 2 illustrates another network model useful with aspects of the invention.

FIG. 2 shows a network model, with a handheld XRF device 211 shown as part of a network. The handheld XRF device of FIG. 2 may be the same as, or similar to, the XRF device of FIG. 1A or FIG. 1B. In the network of FIG. 2, the XRF device 211 communicates with a smartphone 213, which in turn communicates with a smartphone 215 and computers 217a-c. In the network of FIG. 2 the smartphone therefore communicates, with respect to aspects of the invention, with a plurality of compute devices, while in the network of FIG. 1 such communication may be considered to pass through a central server.

Figure 3:
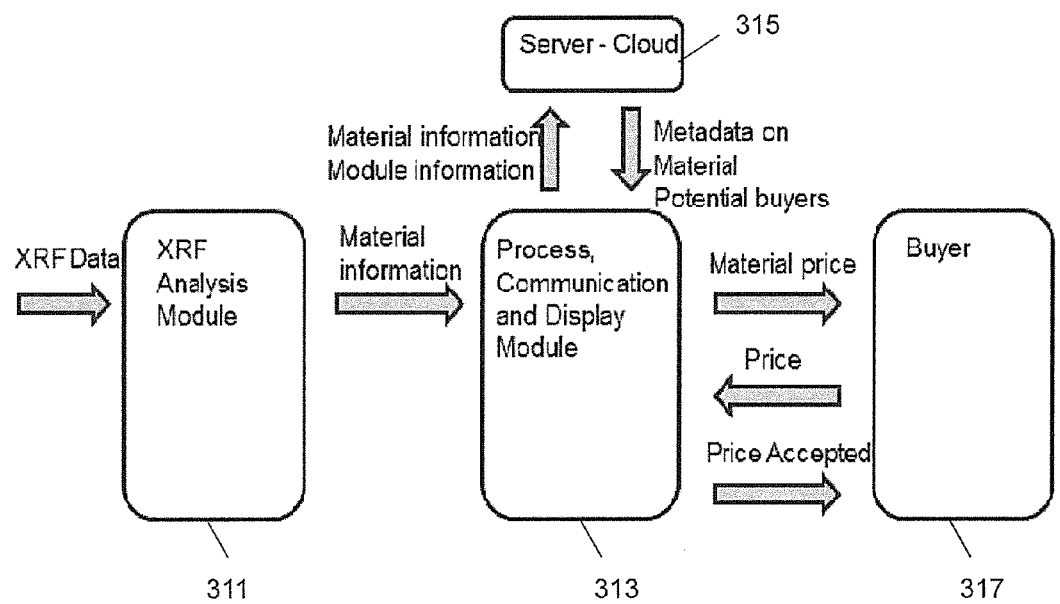
FIG. 3 is a block diagram showing portions of data flow in accordance with aspects of the invention.

FIG. 3 is a block diagram showing portions of data flow in accordance with aspects of the invention. In FIG. 3, XRF detector data is received by an XRF analysis module 311. In most embodiments the XRF analysis module is within a handheld XRF device, for example the XRF device of FIG. 1A. The XRF analysis module determines material composition of a sample, based on the XRF detector data. Information of the material composition is provided to a process, communication, and display module 213, which is in the handheld XRF device in many embodiments. The process, communication, and display module may be in the form of a processor, for example, or may be program instructions executing on a processor, as may be the XRF analysis module. The process, communication, and display module generally formats information for display on a display of the handheld XRF device, provides (and receives) information for communication by communication circuitry of the handheld XRF device, and otherwise processes information.

A server 315, accessible over a communication network, receives information regarding the material composition of the sample, and possibly other information, for example device location and/or information related to a user or entity associated with the device. The server also provides information relating to the material composition and/or potential purchasers of the material composition to the device.

The potential purchasers of the material may include, for example, buyer 317. The process, communication, and display module additionally causes the communication circuitry to communicate with the buyer. The communications may include an identification of the material, a proposed or market price, or other information. The communications may additionally include offers to purchase the material at a particular price from the buyer (or offer to sell at a particular price from the device), and an acceptance of an offer. In some embodiments, the number of buyers may not be limited and may include a number of potential purchasers with access to information provided by the XRF device.

Some aspects of the invention provide a user of a handheld XRF unit metadata, for example including the current price of an identified alloy and information regarding potential buyers for this alloy. Location, for example determined by GPS circuitry of the unit, can be used to identify nearby buyers and the trading history of relevant alloys and/or elements.

In one example, an XRF user identifies a sample as an alloy SS 316 and finds out the closest recycling center that will pay the most for such an alloy.

Aspects of the invention provide additional information to the end user of an analytical instrument, for example an XRF device, given by the connectivity of this instrument. This includes a market making application where sellers can find buyers based on their location and the identified material. Additional metadata will enable higher market knowledge.

Aspects of the invention may be viewed as adding metadata capabilities to an XRF analysis instrument. The result of an analysis can be sent to a server or the cloud where further processing can result in additional information that can be then returned to the user. For example the cost, physical properties, safety data sheet, etc. of a particular alloy and/or the list of identified elements. The location of the user can be used to provide additional information, for example where this same alloy has been sold or identified, where it is manufactured, what it is commonly used for, who is buying it, etc. This information can be logged and recorded at additional locations besides the XRF unit, for example a manager's computer.

Some embodiments of an XRF instrument include a camera. In some embodiments the metadata includes a picture of a sample. Some embodiments of an XRF instrument include printing capabilities to, for example, print out a tag for identified material.

Figure 4:
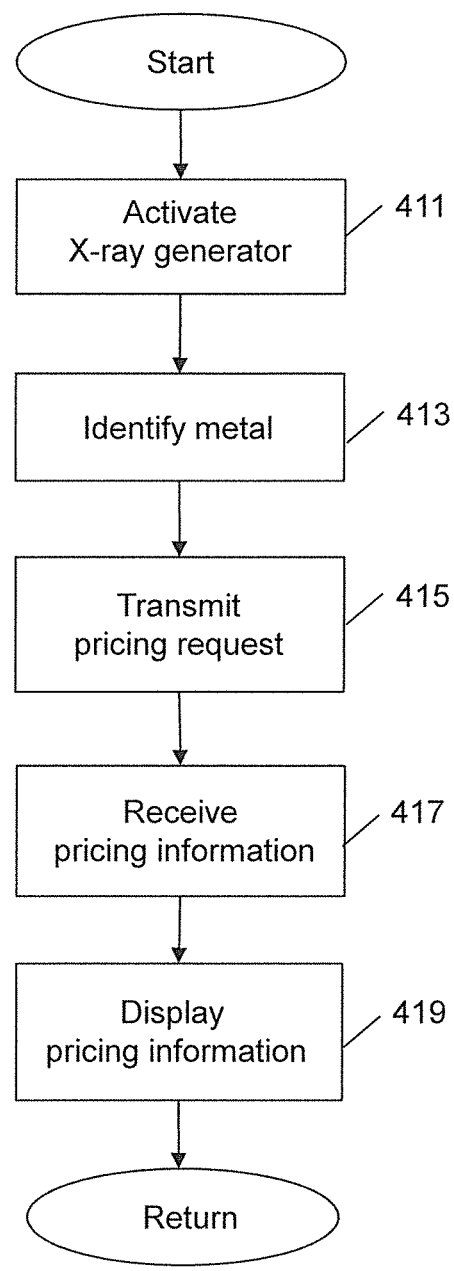
FIG. 4 is a flow diagram of a process useful in providing value information relating to XRF operations.

FIG. 4 is a flow diagram of a process for providing value related information regarding XRF device operations. The process of FIG. 4 may be performed, in some embodiments, by the XRF device and/or smartphone of FIG. 1A, 1B, or 2. In some embodiments the process may be substantially performed by a processor of the XRF device and/or smartphone, with the processor for example configured by program instructions. In some embodiments portions of the process may be partially performed by a server with results/analysis results propagated to one or more XRF devices.

In block 411 the process activates an x-ray generator of an XRF device. In most embodiments the XRF device is a handheld XRF device, and in most embodiments the activation of the x-ray generator is in response to a user input commanding activation of the x-ray generator. In some embodiments, the XRF device is a portable device, which may include a handheld component tied to a main unit. Preferably the XRF device is positioned, or aimed, such that x-rays exiting the device will strike a sample material. The sample material may be or include, for example, a metal or metal alloy.

In block 413 the process identifies a metal or metal alloy of the sample material. In some embodiments the process identifies the metal or metal alloy by receiving a return signal from the sample material and determining a spectrum of the return signal. The return signal is generally generated by x-rays from the x-ray generator striking the sample material. In some embodiments the return signal is received by a detector of the XRF device, and circuitry of the XRF device process information provided by the detector to identify the metal or metal alloy. In some embodiments the circuitry comprises a processor configured by program instructions. In some embodiments the circuitry is of a smartphone in data communication with the XRF device.

In block 415 the process transmits a request for price information for the identified metal or metal alloy. In some embodiments the request includes the identity of the metal or metal alloy. In some embodiments the request is transmitted from the XRF device to the smartphone, and in some embodiments the smartphone forwards, or effectively forwards, the request to a server accessible via a network, which may comprise the Internet. In some embodiments the request is transmitted and/or forwarded by way of cellular communications. In some embodiments the server receives the request, and forwards the request, or sends a similar request to one or more other servers, which may be servers associated with purchasers of metals and/or metal alloys, or which may be servers associated with entities that provide metal and/or metal alloy pricing information. In some embodiments an indication of quantity is transmitted with the request. In some embodiments the indication of quantity is a weight of the sample material. In some embodiments the weight is provided to the XRF device, or the smartphone, by a scale. In some embodiments the scale includes wireless communication circuitry for providing the weight to the XRF device or smartphone. In some embodiments the scale includes wired communication circuitry. In other embodiments the indication of quantity can be entered manually by the user.

In block 417 the process receives pricing information for the identified metal or metal alloy. In some embodiments the pricing information is received from a network comprising the Internet. In some embodiments the pricing information is received by way of a cellular communications capability of the XRF device. In some embodiments the pricing information is received by way of a cellular communications capability of a smartphone. In some embodiments the pricing information is generated by a server, which transmits the pricing information over a network comprising the Internet.

In block 419 the process displays the pricing information. In some embodiments the pricing information is displayed on the smartphone. In some embodiments the pricing information is displayed on a display of the XRF device.

The process thereafter returns.

Figure 5:
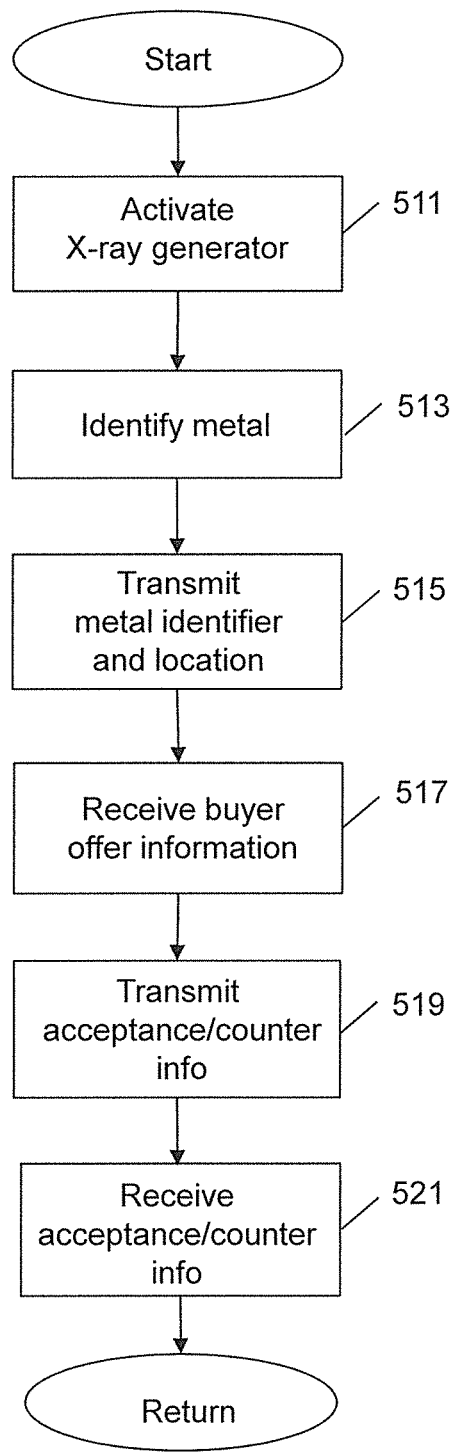
FIG. 5 is a flow diagram of a process useful in completing transactions relating to XRF identified materials.

FIG. 5 is a flow diagram of a process useful in completing transactions relating to XRF identified materials. The process of FIG. 5 may be performed, in some embodiments, by the XRF device and/or smartphone of FIG. 1A, 1B, or 2. In some embodiments the process may be substantially performed by a processor of the XRF device and/or smartphone, with the processor for example configured by program instructions.

In block 511 the process activates an x-ray generator of an XRF device. In most embodiments the XRF device is a handheld XRF device, and in most embodiments the activation of the x-ray generator is in response to a user input commanding activation of the x-ray generator. Preferably the XRF device is positioned, or aimed, such that x-rays exiting the device will strike a sample material. The sample material may be or include, for example, a metal or metal alloy.

In block 513 the process identifies a metal or metal alloy of the sample material. In some embodiments the process identifies the metal or metal alloy by receiving a return signal from the sample material and determining a spectrum of the return signal. The return signal is generally generated by x-rays from the x-ray generator striking the sample material. In some embodiments the return signal is received by a detector of the XRF device, and circuitry of the XRF device process information provided by the detector to identify the metal or metal alloy. In some embodiments the circuitry comprises a processor configured by program instructions. In some embodiments the circuitry is of a smartphone in data communication with the XRF device.

In block 515 the process transmits an identification of the metal or metal alloy and a location of the metal or metal alloy. In some embodiments the location of the metal or metal alloy is determined to be a location of the XRF device, for example at or about the time of activation of the x-ray generator, and in some embodiments the location is based on information from a GPS receiver of the XRF device or a smartphone communicatively coupled to the XRF device. In some embodiments the information is transmitted from the XRF device to the smartphone, and in some embodiments the smartphone forwards, or effectively forwards, the information to a server accessible via a network, which may comprise the Internet. In some embodiments the information is transmitted and/or forwarded by way of cellular communications. In some embodiments the server receives the information, and forwards the information, or sends similar information to one or more other servers, which may be servers associated with purchasers of metals and/or metal alloys. In some embodiments an indication of quantity is transmitted with the information. In some embodiments the indication of quantity is a weight of the sample material. In some embodiments the weight is provided to the XRF device, or the smartphone, by a scale. In some embodiments the scale includes wireless communication circuitry for providing the weight to the XRF device or smartphone.

In block 517 the process receives, over the network, an offer to purchase the metal or metal alloy. In some embodiments information of the offer is displayed on a display of the XRF device or the smartphone. In some embodiments multiple offers are received.

In block 519 the process transmits, over the network, an acceptance of the offer, or alternatively a counter offer, and in block 521 the process receives, over the network, an acceptance of the counter offer or alternatively a further counter offer. The operations of blocks 519 and 521 therefore provide for negotiations over terms of purchase and sale of the identified metal. In some embodiments the acceptance of the offer is based on a user input to the XRF device or smartphone. In some embodiments the counter offer includes information based on a user input to the XRF device or smartphone.

The process thereafter returns.

Figure 6:
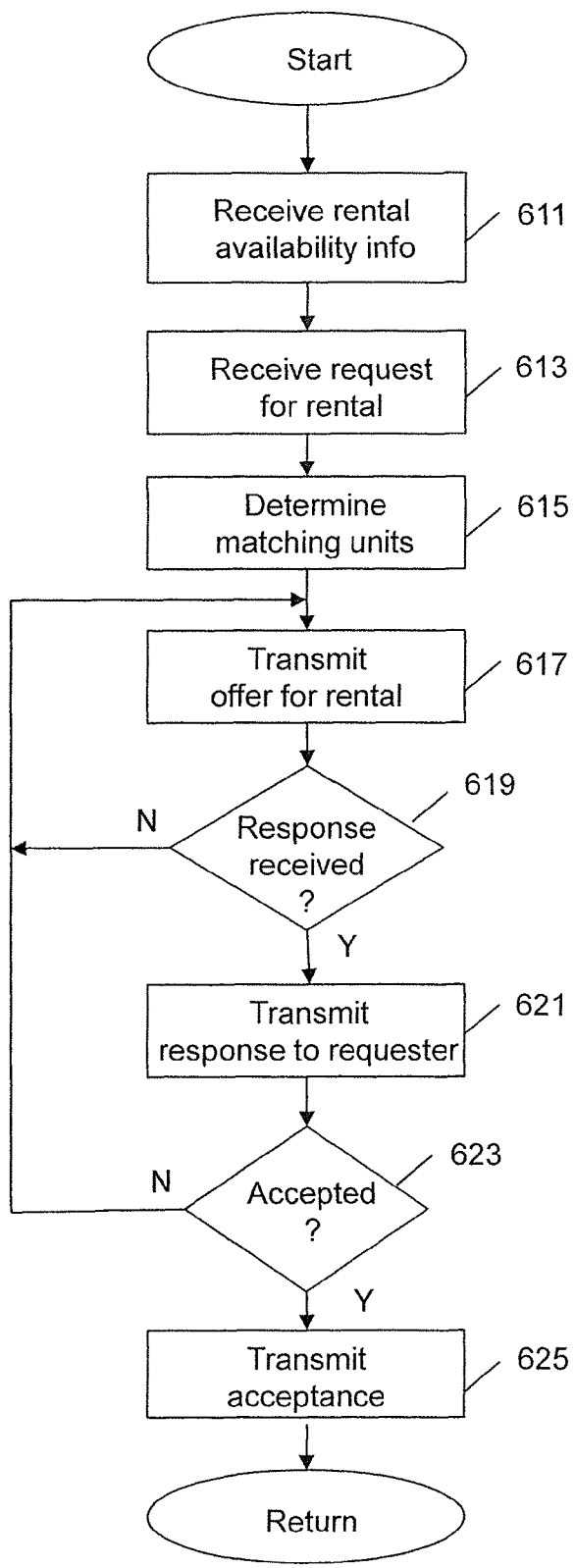
FIG. 6 is a flow diagram of a process useful in increasing XRF device utilization.

FIG. 6 is a flow diagram of a process useful in increasing XRF device utilization. The process of FIG. 6 may be performed, in some embodiments, by the server of FIG. 1 and/or the smartphone of FIG. 2. In some embodiments the process may be substantially performed by a processor of the server and/or smartphone, with the processor for example configured by program instructions.

In block 611 the process receives XRF device availability for rental information. In some embodiments the XRF device availability for rental information includes information as to time of availability, location of the XRF device, and, in some embodiments, price for rental information. In some embodiments XRF device availability for rental information is received for a plurality of XRF devices. In some embodiments the XRF device availability for rental information is received from the XRF devices over a network. In some embodiments the XRF device availability for rental information is received from a smartphone, which in some embodiments is in data communication with the XRF device. In some embodiments the location of the XRF device is based on information provided by a GPS receiver of the XRF device. In some embodiments the location of the XRF device is based on information provided by a GPS receiver of a smartphone, which in some embodiments is in data communication with the XRF device. In some embodiments the location of the XRF device may be provided by low energy Bluetooth, RFID location technology, or other means such as wireless triangulation.

In block 613 the process receives a request for rental of an XRF device. In some embodiments the request includes some or all of information regarding desired rental location, desired rental price, and/or desired XRF device capabilities, manufacturer, or model.

In block 615 the process determines which of the XRF devices available for rental may provide a match for the request for rental. In some embodiments all XRF devices available for rental provide a match for the request for rental. In some embodiments XRF devices within a predetermined distance of the desired rental location provide a match for the request for rental.

In block 617 the process transmits an offer for rental to at least one XRF device and/or smartphone in data communication with the XRF device. In some embodiments the process in block 617 transmits the offer for rental to only a single XRF device or smartphone. In some embodiments the process in block 617 transmits the offer for rental to a plurality of XRF devices and/or smartphones associated with those XRF devices.

In block 619 the process determines if a response to the offer for rental has been received. If not, the process returns to block 617 and transmits the offer for rental to additional XRF devices. Otherwise, the process continues to block 621 and transmits the response to the device from which the offer for rental originated. In block 623 the process determines if the response is an acceptance of the offer for rental. If not, the process returns to block 617 and transmits the offer for rental to additional XRF devices/smartphones. If the response is an acceptance, however, the process continues to block 625, transmits acceptance of the offer, for example both to the requesting device and accepting XRF device/smartphone, and thereafter returns.

Figure 7:
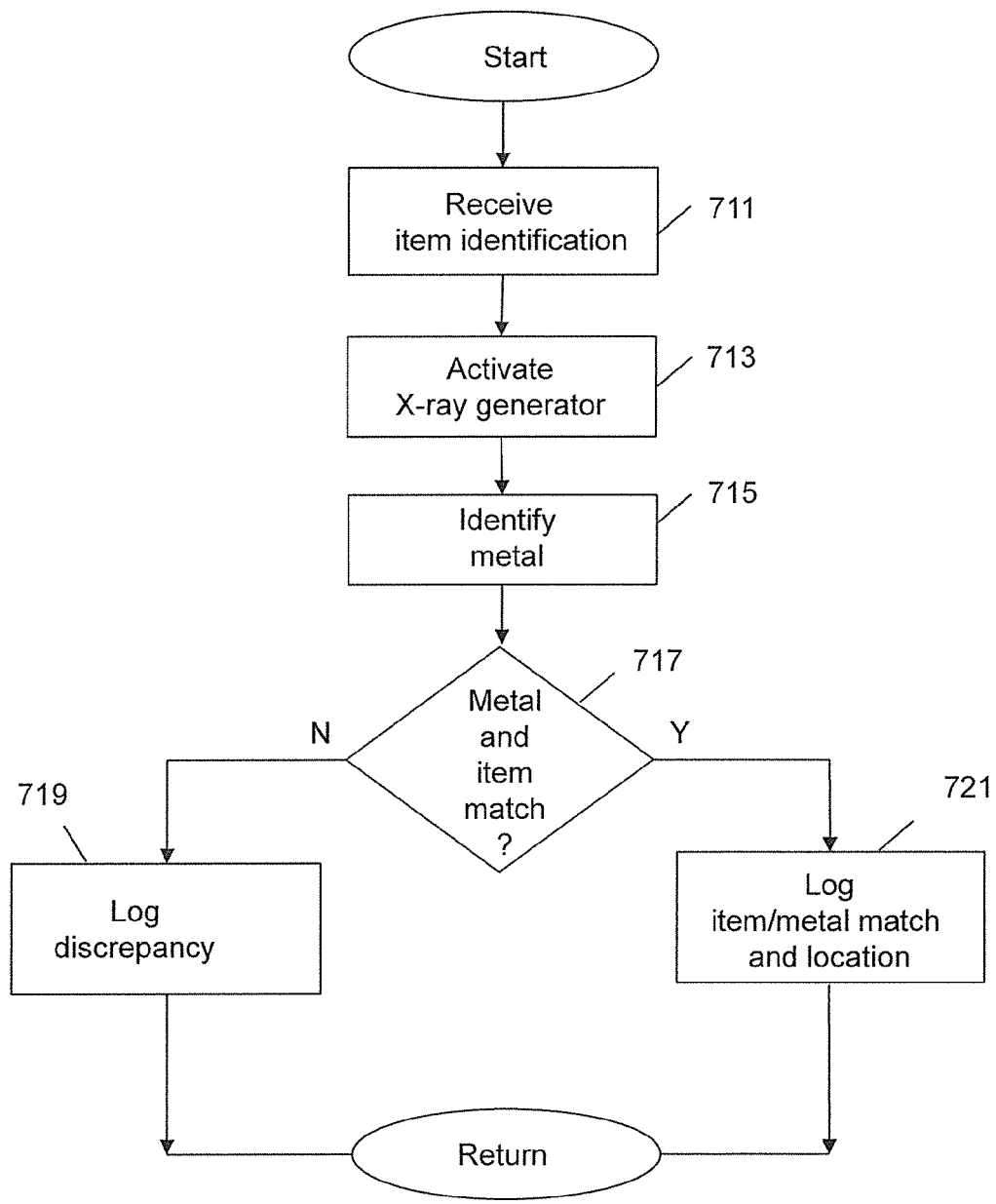
FIG. 7 is a flow diagram of a process useful in tracking materials identified by XRF devices.

FIG. 7 is a flow diagram of a process useful in tracking materials identified by XRF devices. The process of FIG. 7 may be performed, in some embodiments, by the XRF device and/or smartphone of FIG. 1A, 1B or 2. In some embodiments the process may be substantially performed by a processor of the XRF device and/or smartphone, and in some embodiments by a server, with the processor for example configured by program instructions. In some embodiments portions of the process of FIG. 7 may be partially performed by a server, for example the server of FIG. 1B.

In block 711 the process receives an item identification. In some embodiments the item identification is entered into the XRF device, or associated smartphone, by a user. In some embodiments the item identification is received over a network. In some embodiments the item identification includes an identification of material, for example a metal or metal alloy, of the item.

In block 713 the process activates an x-ray generator of the XRF device. In most embodiments the XRF device is a handheld XRF device, and in most embodiments the activation of the x-ray generator is in response to a user input commanding activation of the x-ray generator. Preferably the XRF device is positioned, or aimed, such that x-rays exiting the device will strike the item purportedly identified by the item identification.

In block 715 the process identifies a metal or metal alloy of the item. In some embodiments the process identifies the metal or metal alloy by receiving a return signal from the item and determining a spectrum of the return signal. In some embodiments, the process identification may include elemental analysis for trace element or trace element detection, as well as variances on the make-up or composition of materials under analysis. The return signal is generally generated by x-rays from the x-ray generator striking the item. In some embodiments the return signal is received by a detector of the XRF device, and circuitry of the XRF device process information provided by the detector to identify the metal or metal alloy. In some embodiments the circuitry comprises a processor configured by program instructions. In some embodiments the circuitry is of a smartphone in data communication with the XRF device.

In block 717 the process determines if the material indicated by the item information and the material as indicated by the return signal match. If so, the process continues to block 721 and logs the item/material match, and thereafter returns. If not, the process continues to block 719 and logs the item/material discrepancy.

In some embodiments logging includes storing in memory an indication of match or lack thereof. In some embodiments logging includes storing an indication of some or all of the item identification, the item material as indicated by the return signal, and whether the two match. In some embodiments a time and/or place of activation of the x-ray generator is additionally stored. In some embodiments the time is derived from or by circuitry of the XRF device or smartphone, and in some embodiments the place is determined based on information such as from a GPS receiver of the XRF device or smartphone or other location means. In addition, in some embodiments the XRF device includes a camera activated about time of activation of the x-ray generator, and having a view of the item to be or which was used to generate the return signal, with a resulting image also stored as part of logging of the match/mismatch. In some embodiments the storing in memory is performed by, for example, a server or computer coupled to the server. In such embodiments, the XRF device and/or smartphone may transmit information to be stored to the server by way of a network. In some embodiments the XRF device and/or smartphone may transmit information to be stored to the server by way of hard wire.

Although the invention has been discussed with respect to various embodiments, it should be recognized that the invention comprises the novel and non-obvious claims supported by this disclosure.

What is claimed is:

1. A handheld x-ray fluorescence (XRF) device, comprising:
   an x-ray source;
   a detector for detecting a return signal;
   circuitry for processing the return signal to determine material composition of a sample struck by x-rays of the x-ray source;
   cellular communication circuitry;
   a display; and
   a processor configured by program instructions, the program instructions including program instructions to provide information regarding the material composition of the sample to the cellular communication circuitry for transmission; wherein the program instructions further include program instructions for providing XRF device availability for rental information to the cellular communication circuitry for transmission.

2. The handheld XRF device of claim 1, wherein the XRF device availability for rental information includes time of availability.

3. The handheld XRF device of claim 1, further comprising a GPS receiver, and wherein the XRF device availability for rental information includes location of the XRF device.

4. The handheld XRF device of claim 1, wherein the XRF device availability for rental information includes price for rental information.

5. A method of operation of a handheld x-ray fluorescence (XRF) device, comprising:
   activating an x-ray source of the handheld XRF device;
   detecting a return signal;
   processing the return signal to determine material composition of a sample struck by x-rays of the x-ray source;
   providing information regarding the material composition of the sample to communication circuitry for transmission;
   transmitting the information regarding the material composition of the sample over a network;
   receiving information regarding pricing of the sample, and displaying the information regarding pricing of the sample by a display of the XRF device.

6. The method of claim 5, wherein the information regarding the material composition of the sample comprises an identification of the material composition of the sample.

7. The method of claim 6, further comprising providing a location of the sample along with the identification of the material composition of the sample to the communication circuitry for transmission and transmitting the location of the sample over the network.

8. The method of claim 7, further comprising providing an indication of quantity of the sample to the communication circuitry for transmission and transmitting the indication of quantity of the sample over the network.

9. The method of claim 8, wherein the indication of quantity is a weight.

10. The method of claim 5, further comprising providing XRF device availability for rental information to the communication circuitry for transmission and transmitting the XRF device availability for rental information.

11. The method of claim 10, wherein the XRF device availability for rental information includes time of availability.

12. The method of claim 10, wherein the XRF device availability for rental information includes location of the XRF device.

13. The method of claim 9, wherein the XRF device availability for rental information includes price for rental information.

14. The method of claim 5, further comprising determining if the information regarding the material composition of the sample matches an item identification.

15. The method of claim 14, further comprising storing a result of the determination of whether the material composition of the sample matches the item identification.

16. The method of claim 15, further comprising storing a time and/or place of activation of the x-ray source.

17. A method of providing handheld x-ray fluorescence (XRF) device rental availability information, comprising:
   receiving an indication of XRF device location;
   receiving an indication of XRF device rental price;
   receiving an indication of XRF device time of availability;
   transmitting, by the XRF device, the XRF device location, XRF device rental price, and XRF device time of availability over a network.

18. The method of claim 17, wherein the indication of XRF device location is received from a GPS receiver of the XRF device.

* * * * *